(12) United States Patent
Ivashin et al.

(10) Patent No.: US 9,857,336 B1
(45) Date of Patent: Jan. 2, 2018

(54) MULTI-CHANNEL ION MOBILITY SPECTROMETER

(71) Applicant: Implant Sciences Corporation, Wilmington, MA (US)

(72) Inventors: Dmitriy V. Ivashin, Peabody, MA (US); Anatoly Lazerevich, Newton, MA (US); Said Boumsellek, San Diego, CA (US)

(73) Assignee: L3 Technologies, Inc., Wilmington, MA (US)

( * ) Notice: Subject to any disclaimer, the term of this patent is extended or adjusted under 35 U.S.C. 154(b) by 0 days.

(21) Appl. No.: 15/218,308

(22) Filed: Jul. 25, 2016

Related U.S. Application Data

(60) Provisional application No. 62/195,986, filed on Jul. 23, 2015.

(51) Int. Cl.
 *H01J 49/26* (2006.01)
 *G01N 27/62* (2006.01)
 *H01J 49/00* (2006.01)

(52) U.S. Cl.
 CPC ........ *G01N 27/622* (2013.01); *H01J 49/0031* (2013.01)

(58) Field of Classification Search
 CPC .... H01J 49/00; H01J 49/0009; H01J 49/0013; H01J 49/0018; H01J 49/0022; H01J 49/0027; H01J 49/0031; H01J 49/0036; H01J 49/02; H01J 49/022; H01J 49/06; H01J 49/065; H01J 49/066; H01J 49/426
 USPC ........ 250/281, 282, 283, 290, 291, 292, 293
 See application file for complete search history.

(56) References Cited

U.S. PATENT DOCUMENTS

| | | | |
|---|---|---|---|
| 2013/0009051 A1* | 1/2013 | Park ...................... | H01J 49/063 250/282 |
| 2013/0161506 A1* | 6/2013 | Ugarov .................. | G01N 27/62 250/282 |
| 2014/0239174 A1* | 8/2014 | Anderson ............. | G01N 27/622 250/288 |
| 2014/0260702 A1* | 9/2014 | Benner ................ | G01N 15/0266 73/865.5 |
| 2016/0005581 A1* | 1/2016 | Graichen .............. | G01N 27/622 250/282 |

* cited by examiner

*Primary Examiner* — Nicole Ippolito
(74) *Attorney, Agent, or Firm* — Muirhead and Saturnelli, LLC

(57) ABSTRACT

An ion mobility spectrometer includes a drift tube, a plurality of sensors arranged at one end of the drift tube that provide signals corresponding to ions impinging on the sensors, and a multi-channel data acquisition system, coupled to each of the sensors, that compensates for delays experienced by ions that are farther from a main axis of drift tube prior to combining the signals from the sensors. The sensors may be electrically biased so that a particular one of the sensors that attracts ions is adjacent to one or more of the sensors that do not attract ions. Signals from adjacent sensors may be subtracted to reduce signal values corresponding to mirror current. The plurality of sensors may be arranged as a honeycomb or as a plurality of concentric circles.

10 Claims, 4 Drawing Sheets

MULTI-CHANNEL ION MOBILITY SPECTROMETER

CROSS-REFERENCE TO RELATED APPLICATIONS

This application claims priority to U.S. Provisional App. No. 62/195,986, filed on Jul. 23, 2015, entitled "HIGH PERFORMANCE MULTI-CHANNEL ION MOBILITY SPECTROMETER", which is incorporated herein by reference.

TECHNICAL FIELD

This application is related to the field of chemical analysis and, in particular, ion mobility spectrometry.

BACKGROUND OF THE INVENTION

Ion mobility spectrometry is widely used as a simple low cost highly sensitive chemical analysis technique in trace explosives and narcotics screening applications by separating and identifying ionized molecules in the gas phase based on mobility of the ionized molecules. An ion mobility spectrometer (IMS) uses an ionization source, a drift tube, and an ion collector to detect the ionized molecules. The drift tube of an IMS is provided by a stack of rings on which a voltage schedule is applied in order to establish an axial field to move the ions from the ionization source to the detector. The detector consists of an ion collector (solid Faraday plate) and an amplifier stage converting incoming ion charge to a voltage that can be digitized for further processing.

FIG. 1 illustrates an issue with a conventional IMS relating to the presence of radial variations in the electric field in the drift tube. The electric field lines are shown in FIG. 1. The drift field becomes progressively less homogeneous according to a distance from a main axis (central axis) of the drift tube. Any inhomogeneity in the electric field will cause a drift delay relative to an ion which experiences a perfectly uniform field. Field equipotential values are relatively straight near the main axis of the tube but become more distorted as the distance from the main axis increases. As a result, ions of identical mobility values moving near the edge of the drift tube will have a drift time different from that of ions moving near the main axis. This causes broadening of IMS peaks and therefore loss of resolving power. The greater the inhomogeneity in the electric field, the greater the difference in drift time and therefore the broader the IMS peak. Field distortions are also observed near the detector.

The distortion may be addressed by using a detector plate that is significantly smaller in diameter than the diameter of the drift tube. Although this improves resolving power of the IMS, using a relatively small diameter detector reduces sensitivity of the IMS by collecting fewer ions. The diameter of the collector plate for an IMS is a trade-off between resolution and sensitivity; the collector plate is small enough to collect only ions near the main axis but large enough to collect as many ions as possible in order to achieve good sensitivity.

In addition, for stand-alone IMS instruments, a charge is induced in the collector by the cloud of ions near the collector. The charge, when integrated over time, corresponds to a so called mirror current. The mirror current is undesirable because it leads to reduced resolving power by artificially broadening the detected width of the ion signals. The mirror current in an IMS may be addressed using an aperture grid (AG), which is a metal mesh placed at a distance 0.3 to 3 mm from the collector and biased with a voltage to act as an electrical shield. The AG prevents induced current flow in the detector caused by the approach of the cloud of ions. However, while the AG provides a solution to the mirror current problem, use of the AG reduces instrument sensitivity because many ions are annihilated when striking the wires of the mesh. In order to minimize ions losses, the mesh may be designed for high transparency using very thin wire. This makes the mesh relatively fragile and subject to distortions and damage due to vibrations and shock encountered by IMS instruments used in the field.

Accordingly, it is desirable to provide advantageous and efficient techniques that address the relatively small diameter used for the collector plate as well as eliminating the need for an aperture grid.

SUMMARY OF THE INVENTION

According to the system described herein, an ion mobility spectrometer, includes a drift tube, a plurality of sensors arranged at one end of the drift tube, that provide signals corresponding to ions impinging on the sensors, and a multi-channel data acquisition system, coupled to each of the sensors, that compensates for delays experienced by ions that are farther from a main axis of drift tube prior to combining the signals from the sensors. The sensors may be electrically biased so that a particular one of the sensors that attracts ions is adjacent to one or more of the sensors that do not attract ions. Signals from adjacent sensors may be subtracted to reduce signal values corresponding to mirror current. The plurality of sensors may be arranged as a honeycomb or as a plurality of concentric circles. The multi-channel data acquisition system may be a programmable system-on-chip platform that offers software, hardware and I/O programmability in a single chip.

According further to the system described herein, detecting ions from a plurality of sensors in drift tube of an ion mobility spectrometer includes time shifting each signal according to a distance of a corresponding sensor from a main axis of the drift tube, multiplying each of the values of each signal from the sensors by a constant value, and determining a combined signal value by summing a result multiplying each of the values of each signal. Time shifting may include providing an amount of delay that varies according to a distance of each of the sensors from the main axis of the drift tube. An amount of the time shift may be determined empirically using known substances. The constant value may be one for all of the sensors.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

The system described herein enhances the selectivity and sensitivity of field deployable ion mobility spectrometers while, at the same time, eliminating the need for an aperture grid by using position sensitive discrete detectors and a multi-channel simultaneous sampling data acquisition system to produce ion mobility spectra with sensitivities and resolving powers approaching and exceeding those of large bulky laboratory-type devices. The system described herein compensates for drift time delays associated with field non-uniformities within the drift tube and provides a large segmented ion collector, configured as a honeycomb structure or radial concentric rings or bands or similar structure to detect ions distributed transversally (radially) along a cross section of the IMS drift tube. Enlarging and segmenting the detection area increases overall sensitivity while providing ways to measure and compensate for drift time delays and hence peak broadening associated with field non-uniformities. Using a large bandwidth multi-channel data acquisition system, multiple ion mobility spectra are produced simultaneously and processed in real time using time-shift and deconvolution algorithms. The multi-channel data acquisition system may be based on an all Programmable System-on-Chip platform that offers software, hardware and I/O programmability in a single chip. The system may incorporate a multi-core ARM CPU and programmable logic (Field-Programmable Gate Array) enabling a small footprint and low power circuitry, simultaneous multi-channel data acquisition, high-speed data transfer between FPGA and CPU utilizing DMA engine (Direct Memory Access) hence freeing the CPU to perform other tasks, high-frequency high-resolution control signals for the drift tube electronics such as drift voltage and Ion Gating Circuitry, high computing power for processing ion mobility spectra using advanced algorithms in real time, and hardware accelerated encryption for sensitive data.

Other advantages of using a segmented ion collector include simplifying and therefore reducing the cost of the drift tube by removing elements such as the aperture grid. Using a segmented ion collector, the mirror current may be measured on separate ion collectors and therefore subtracted out to get the original shape and width of the ion peak and cancel out the mirror current component. Thus the system described herein enables the removal of the aperture grid to provide a simpler drift tube design with no peak broadening due to the mirror current. Using the multi-channel data acquisition, the measurement and subtraction of the mirror current may be performed in real time.

Figure 1:
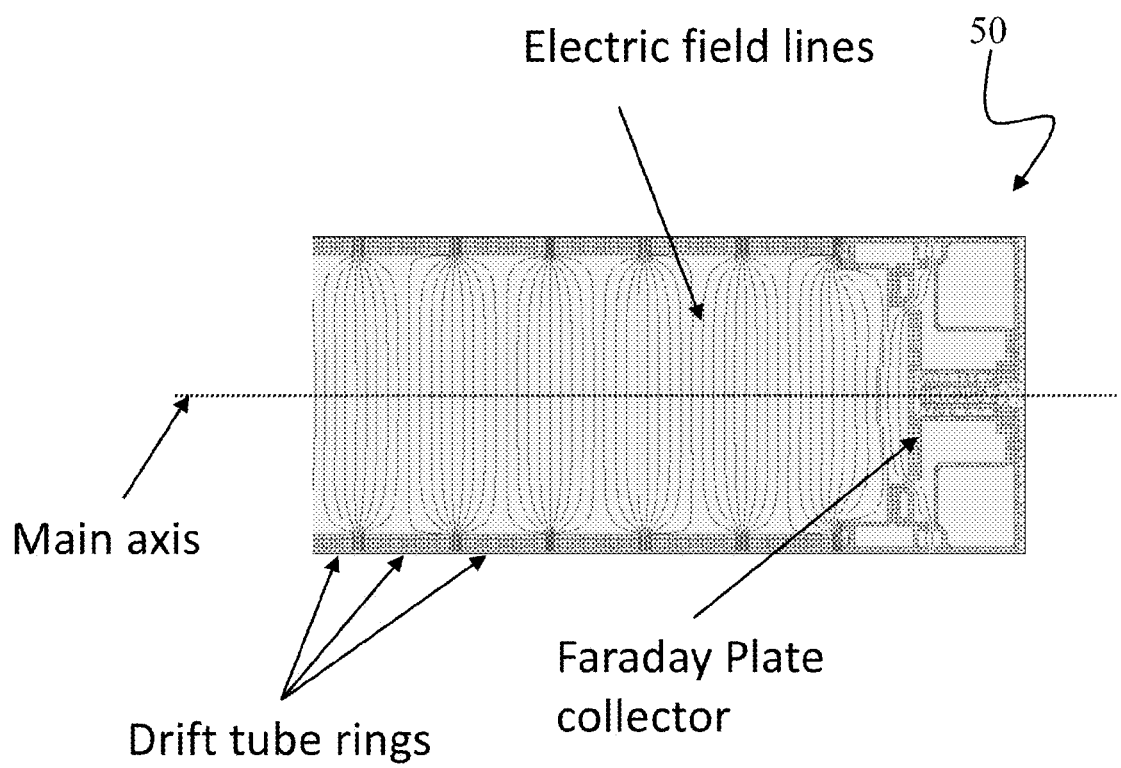
FIG. 1 illustrates electric field lines in a drift tube of a conventional ion mobility spectrometer.
Figure 2:
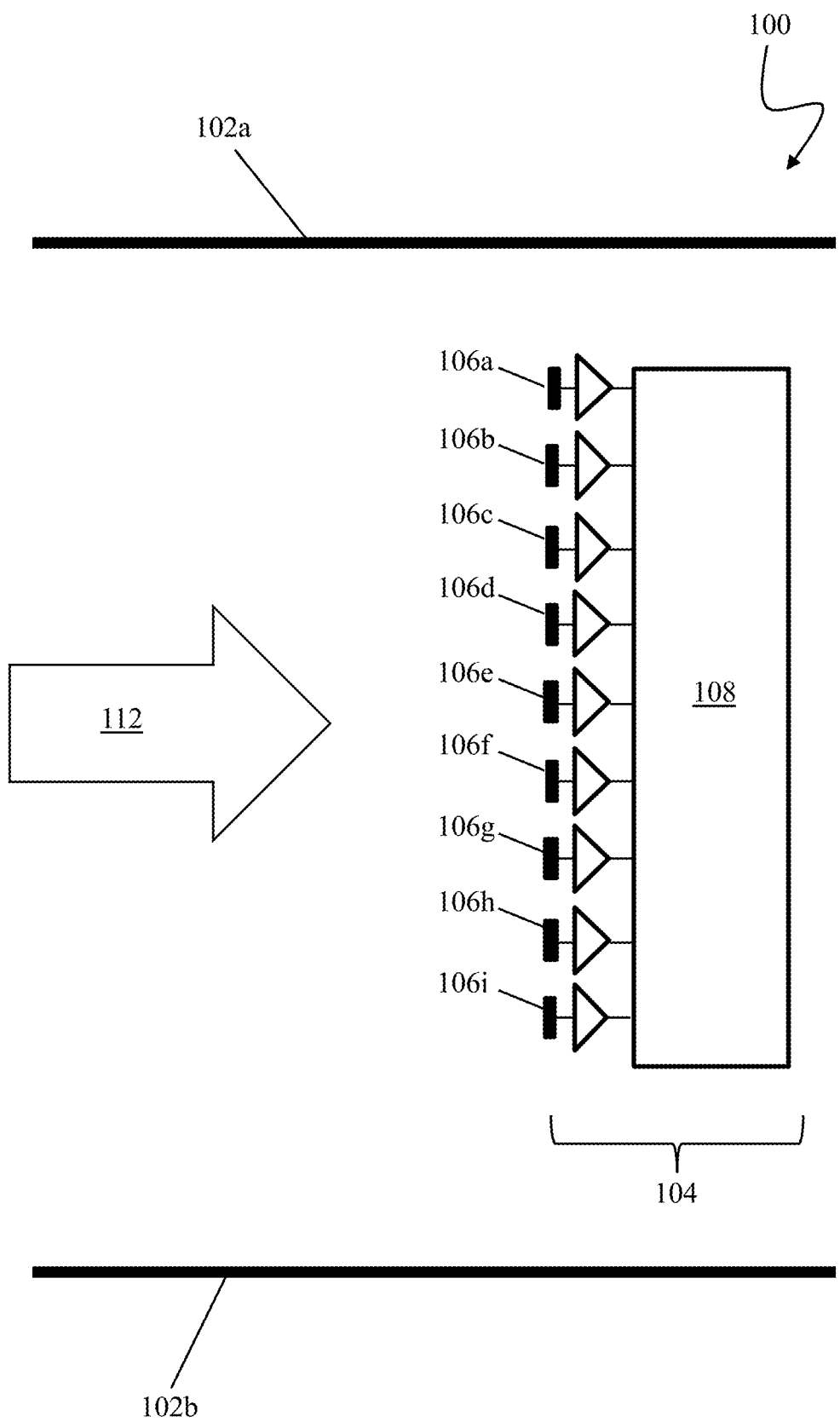
FIG. 2 is a schematic illustration showing a multi-channel ion mobility spectrometer according to an embodiment of the system described herein.

Referring to FIG. 2, a portion of an IMS includes a drift tube walls 102a, 102b and a multi-channel detector 104. The IMS also includes an ionization source (or similar), which is not shown in FIG. 2. The multi-channel detector 104 has a plurality of detector plates 106a-106i that are coupled to a multi-channel data acquisition system 108 via a plurality of amplifiers. Electric fields provided by conventional components (not shown) of the drift tube walls 102a, 102b cause ions to move in a direction indicated by an arrow 112 toward the multi-channel detector 104 to impinge on the detector plates 106a-106i. The resulting signals from each of the detector plates 106a-106i are provided to the multi-channel data acquisition system 108 for further processing, including providing compensation for delays experienced by ions that are farther from the main axis of drift tube prior to combining the signals, as explained in more detail elsewhere herein.

The multi-channel data acquisition system 108 may be a programmable system-on-chip platform that offers software, hardware and I/O programmability in a single chip. The system may incorporate a multi-core ARM CPU and programmable logic (Field-Programmable Gate Array) enabling a small footprint and low power circuitry, simultaneous multi-channel data acquisition, high-speed data transfer between FPGA and CPU utilizing DMA engine (Direct Memory Access), freeing the CPU to perform other tasks, high-frequency high-resolution control signals for the drift tube electronics such as drift voltage and Ion Gating Circuitry, high computing power for processing ion mobility spectra using advanced algorithms in real time, and hardware accelerated encryption for sensitive data. The multi-channel data acquisition system 108 may be implemented using conventional components, such as discrete components or a combination of discrete components and one or more single chip multi-channel data acquisition systems, such as the ADAS3022 device provided by the Analog Devices Corporation.

The sensors 106a, 106i that are furthest from the main axis from the drift tube detect ions that experience the greatest delay because the sensors 106a, 106i are furthest from the main axis of the drift tube of the IMS. The sensors 106b, 106h detect ions that experience the second greatest delay, the sensors 106c, 106g detect ions that experience the third greatest delay, and so on. Thus, the multi-channel data acquisition system 108 provides the greatest time delay compensation for signals from the sensors 106a, 106i, the second greatest time delay compensation for signals from the sensors 106b, 106h, and so on. Generally, the signals from the sensors 106a-106i may be combined into a single signal, S, using the following formula:

$$S = A_0 S_0(t_0) + A_1 S_1(t_1) + A_2 S_2(t_2) + \ldots A_n S_n(t_n)$$

where $A_0, A_1, A_2, \ldots A_n$ are constants, $S_0, S_1, S_2, \ldots S_n$ are signal values detected at the different sensors, and $t_0, t_1, t_2, \ldots t_n$ are different time values that take into account the increase in delay of ion drift time for ions that do not travel along the main axis of the ion drift tube. If to is the time at which a signal is measured at a sensor(s) in the center of the collector and therefore on the main axis of the drift tube, the other times will be $t_0 + \delta$, where $\delta$ is a positive value. That is, the other times will be after the time that the signal is obtained at the sensor on the main axis of the drift tube.

Values for $A_0, A_1, A_2, \ldots A_n$ and $t_0, t_1, t_2, \ldots t_n$ may be determined empirically by measurement using known ions to calibrate the system. In some cases, $A_0, A_1, A_2, \ldots A_n$ would all be one (i.e., there would be no constant multipliers for the signal values), so that only the relative time differences between $t_0, t_1, t_2, \ldots t_n$ is determined for calibration purposes.

Figure 3:
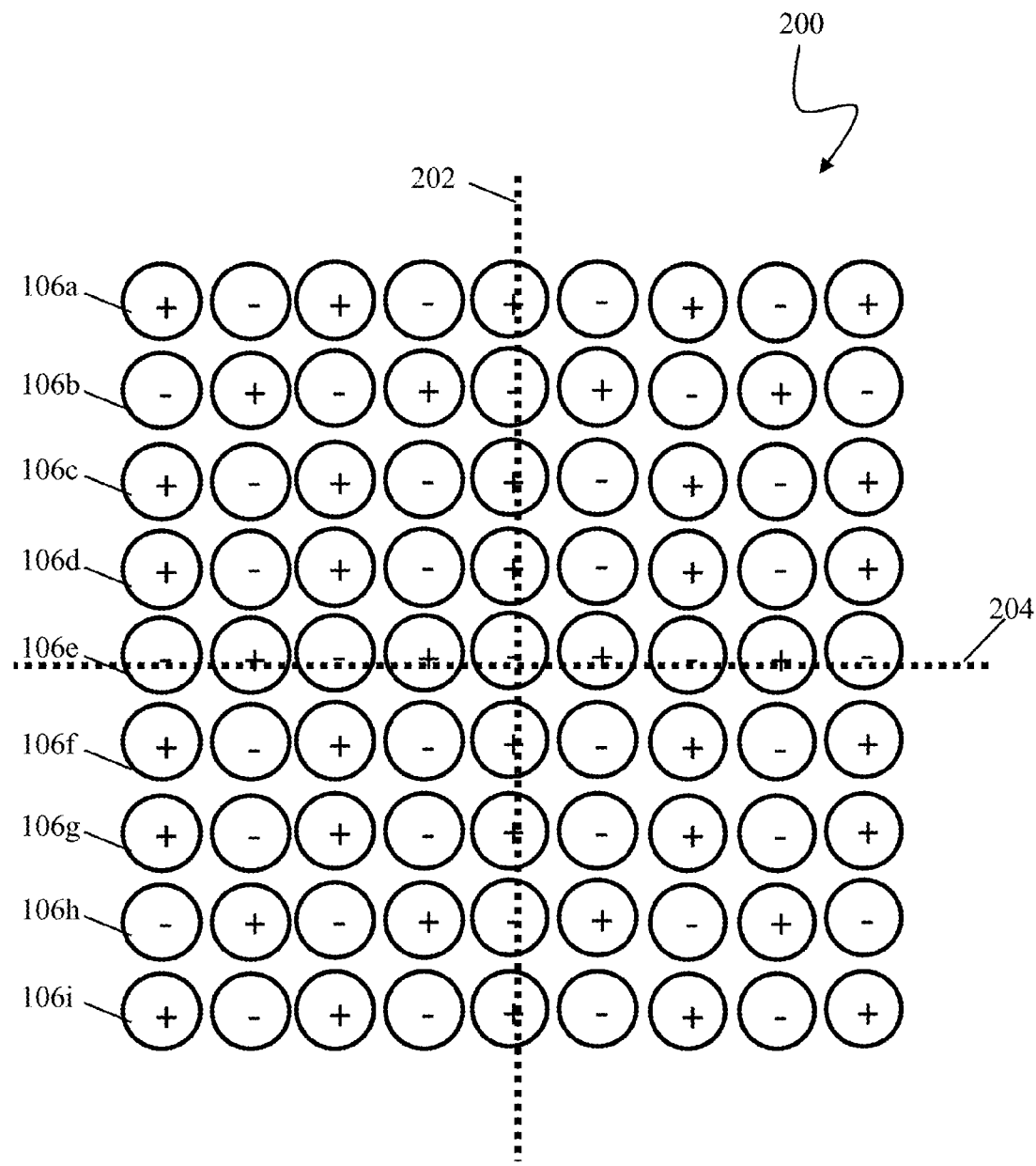
FIG. 3 is a schematic illustration showing a honeycomb sensor array of an ion mobility spectrometer according to an embodiment of the system described herein.

Referring to FIG. 3, a schematic diagram 200 shows the sensors 106a-106c provided in a honeycomb configuration in which the direction of ion drift is orthogonal to that of the diagram 100 of FIG. 2. For the diagram 200, the direction of ion flow is perpendicular to the plane of the diagram 200. A vertical axis 202 is provided at a midpoint between horizontal extremities of the drift tube. Similarly, a horizontal axis 204 is provided at a midpoint between top and bottom extremities of the drift tube. The axes 202, 204 intersect at the main axis of the drift tube.

Each of the individual ones of the sensors is labeled with a "+" or a "−" indicating a relative electrical bias thereof. Ions that travel through the drift tube are attracted to one set of the sensors (e.g., the "+" sensors), but not the other set of the sensors (e.g., the "−" sensors). Although all of the sensors experience a so-called "mirror current" due to a charge induced in the sensors by the cloud of ions near the sensors, only one set of the sensors (e.g., the "+" sensors) attract the ions provide a signal based on detected ions. Thus, the mirror current may be eliminated by determining a difference in signals between one set of sensors and the other set of sensors.

In one embodiment, the mirror current may be eliminated by connecting all of the "+" sensors together and by separately connecting all of the "−" sensors together. The results thereof may be input into a two channel data acquisition system that determines a difference between the channel signals to eliminate the mirror current. In another embodiment, signals from each of the sensors, or possibly signals from relative small groups of sensors (e.g., four at a time) with the same electrical bias (e.g., "+" or "−") are provided as input to a multi-channel data acquisition system 108 like the multi-channel data acquisition system 108, describe in connection with FIG. 2, which subtracts signal values from adjacent sensors or adjacent groups of sensors. Note that the configuration illustrated by the diagram 200 may both provide for multi-channel input that compensates for different drift times and eliminates the need for an aperture gate.

Figure 4:
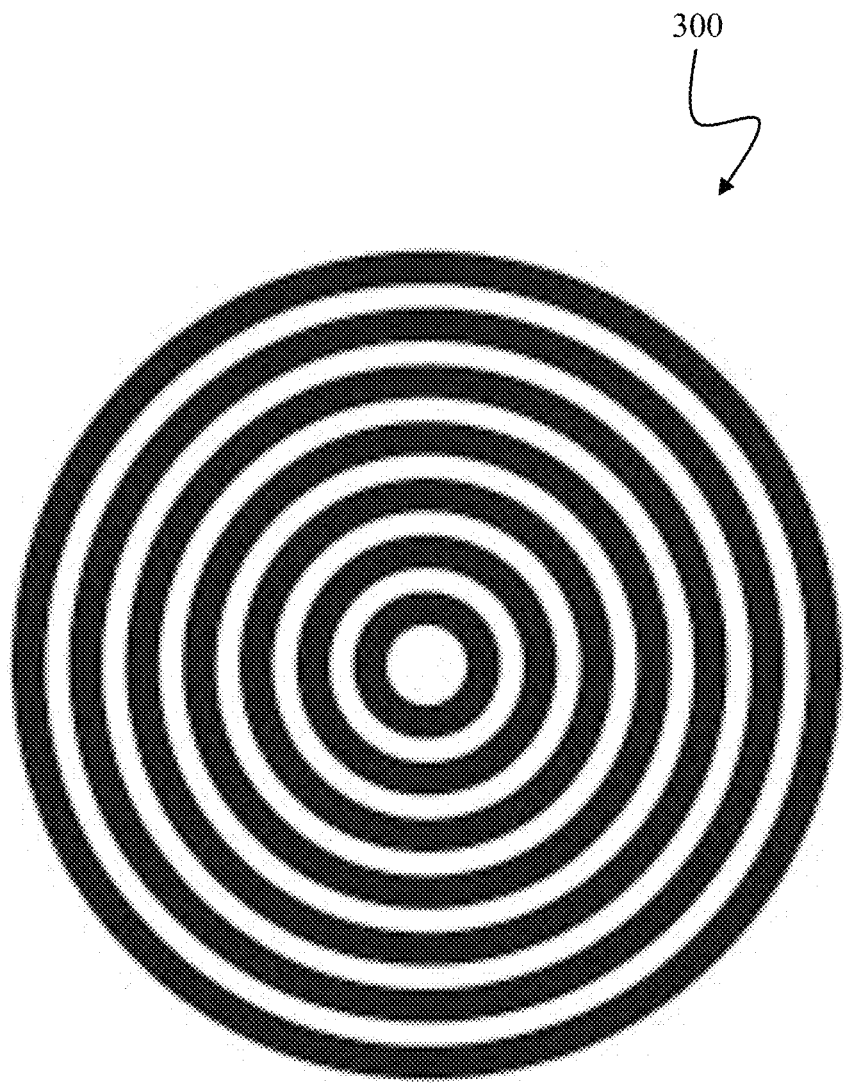
FIG. 4 is a schematic illustration showing a concentric circle sensor array of an ion mobility spectrometer according to an embodiment of the system described herein.

Referring to FIG. 4, a schematic diagram 300 illustrates an embodiment having a plurality of sensors (in white) configured as concentric circles. For the diagram 300, the direction of ion flow is perpendicular to the plane of the diagram 300. Each of the circles may be alternatively biased so that if one of the circles is positively biased (e.g., a "+" sensor), adjacent circles are negatively biased (e.g., are "−" sensors) and vice versa. Just as with the configuration illustrated by the diagram 200, the configuration illustrated by the diagram 300 may both provide for multi-channel input that compensates for different drift times and eliminates the need for an aperture gate.

Note that, in some instances, it is possible to dynamically configure the system to use only a subset of the signals. For example, when a relatively large number of ions are present, it may be possible to not use some of the sensors that are farthest away from the main axis of the drift tube. In some cases, such as when the number of ions is exceptionally large, it may be possible to use only a single central sensor that corresponds to the main axis of the drift tube. Also note that other shapes/configurations of sensors are possible, such as arranging discrete sensors radially from a central axis.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. The system may further include a display and/or other computer components for providing a suitable interface with a user and/or other computers.

In connection with applicable control processing, software used for implementations of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An ion mobility spectrometer, comprising:
   a drift tube;
   a plurality of sensors arranged at one end of the drift tube, that provide signals corresponding to ions impinging on the sensors; and
   a multi-channel data acquisition system, coupled to each of the sensors, that compensates for delays experienced by ions that are farther from a main axis of drift tube prior to combining the signals from the sensors.

2. An ion mobility spectrometer, according to claim 1, wherein the sensors are electrically biased so that a particular one of the sensors that attracts ions is adjacent to one or more of the sensors that do not attract ions.

3. An ion mobility spectrometer, according to claim 2, wherein signals from adjacent sensors are subtracted to reduce signal values corresponding to mirror current.

4. An ion mobility spectrometer, according to claim 1, wherein the plurality of sensors are arranged as a honeycomb.

5. An ion mobility spectrometer, according to claim 1, wherein the plurality of sensors are arranged as a plurality of concentric circles.

6. An ion mobility spectrometer, according to claim 1, wherein the multi-channel data acquisition system is a programmable system-on-chip platform that offers software, hardware and I/O programmability in a single chip.

7. A method of detecting ions from a plurality of sensors in drift tube of an ion mobility spectrometer, comprising:
   time shifting each signal according to a distance of a corresponding sensor from a main axis of the drift tube;
   multiplying each of the values of each signal from the sensors by a constant value; and
   determining a combined signal value by summing a result multiplying each of the values of each signal.

8. A method, according to claim 7, wherein time shifting includes providing an amount of delay that varies according to a distance of each of the sensors from the main axis of the drift tube.

9. A method, according to claim 8, wherein an amount of the time shift is determined empirically using known substances.

10. A method, according to claim 7, wherein the constant value is one for all of the sensors.

* * * * *